United States Patent [19]

Barthel

[11] 4,333,470

[45] Jun. 8, 1982

[54] OUTPUT PULSE ARTIFACT REJECTION IN DEMAND PACEMAKERS

[75] Inventor: Thomas C. Barthel, Becker, Minn.

[73] Assignee: Medtronic, Inc., Minneapolis, Minn.

[21] Appl. No.: 137,578

[22] Filed: Apr. 7, 1980

[51] Int. Cl.³ ............................................ A61N 1/36
[52] U.S. Cl. ............................................ 128/419 PG
[58] Field of Search ................................ 128/419 PG

[56] References Cited

U.S. PATENT DOCUMENTS 3,498,288  3/1970  Max et al. ............................ 128/731
3,661,158  5/1972  Berkovits ........................ 128/419 PG
3,911,929  10/1979 Gobell ............................ 128/419 PG Primary Examiner—William E. Kamm Attorney, Agent, or Firm—Merchant, Gould, Smith, Edell, Welter & Schmidt

[57] ABSTRACT

An atrial-ventricular demand pacemaker having improved atrial pulse artifact rejection includes a blanking circuit (30, 100) connected in the signal path from the ventricular output terminal (17) to the sensing amplifier (21) to blank the signal during an atrial pulse. A holding circuit including a low-pass filter (46, 137) and a switching element (43, 112) stores a prior signal value at the sensing amplifier input during the blanking interval, and delays return to normal operation until after the blanking circuit has returned to normal. Artifact rejection is also improved by limiting atrial pulse output circuit recharge time and by limiting polarization current driven into the ventricular output circuitry by an atrial output pulse.

8 Claims, 4 Drawing Figures

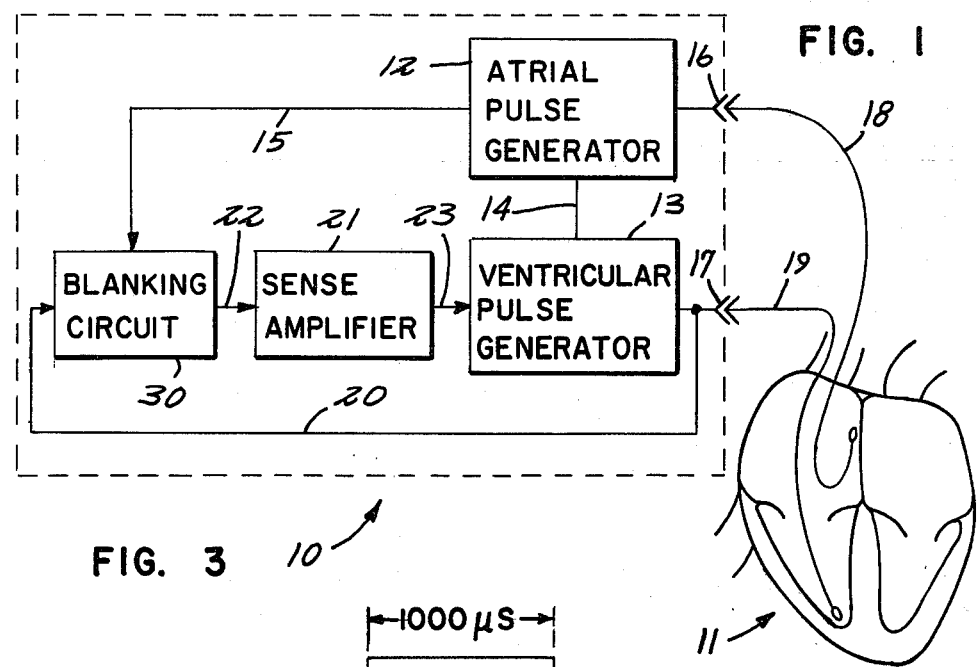
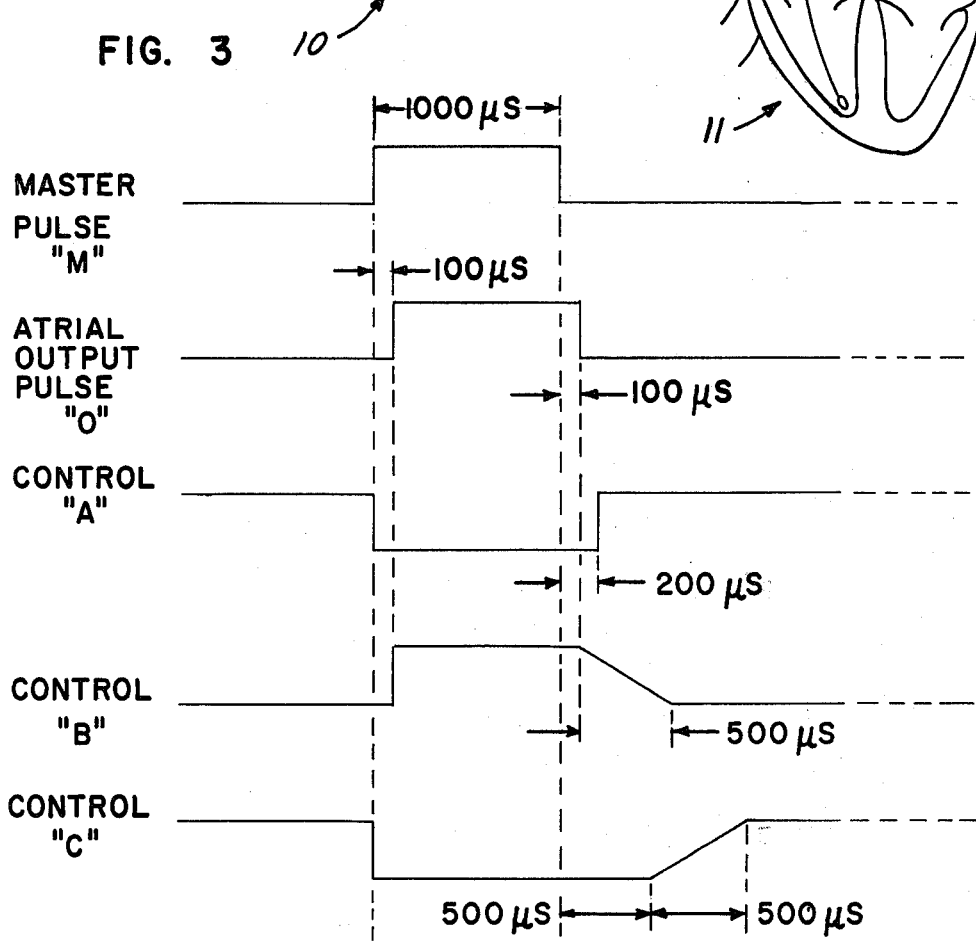

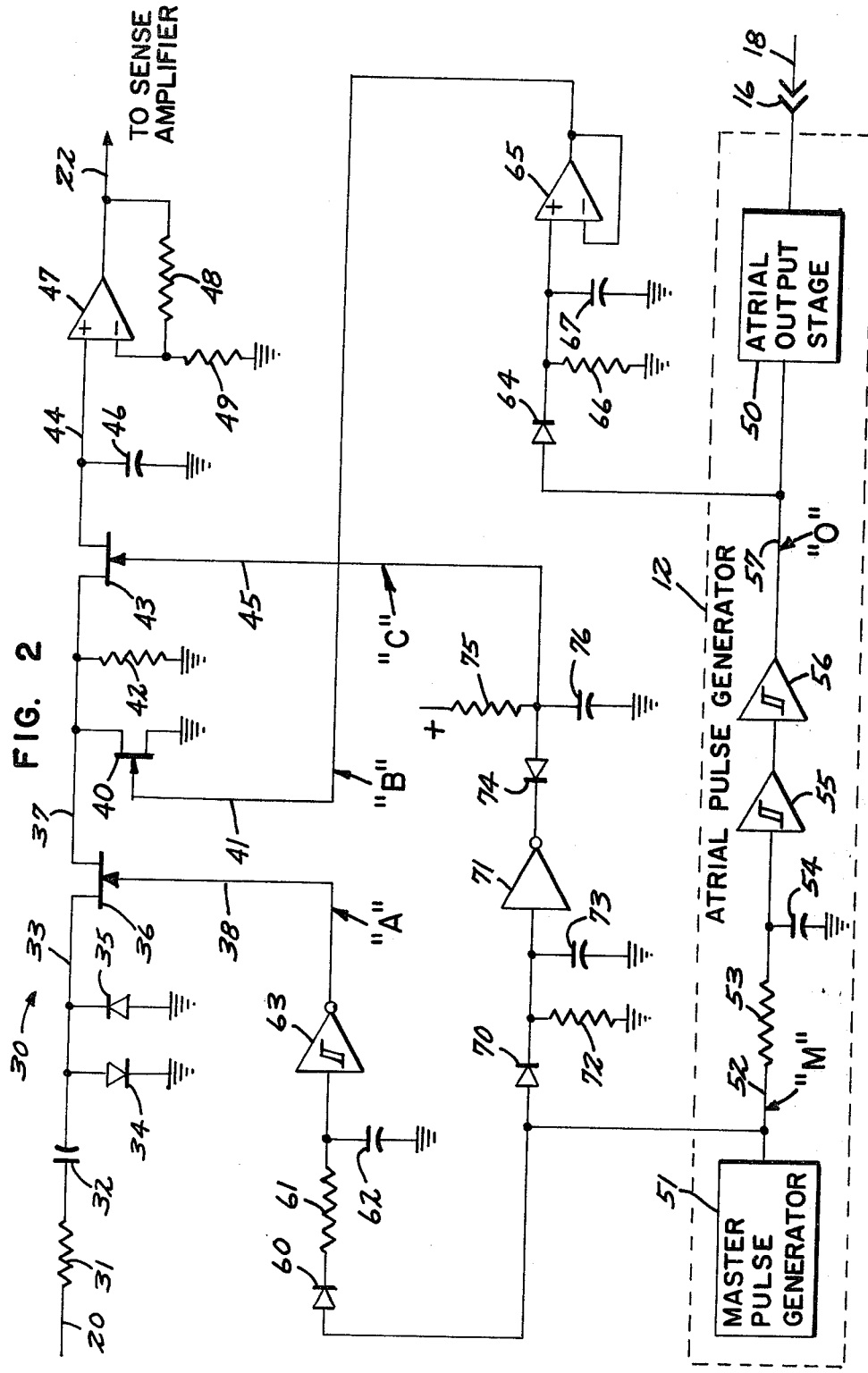

OUTPUT PULSE ARTIFACT REJECTION IN DEMAND PACEMAKERS

TECHNICAL FIELD OF THE INVENTION

This invention pertains to the field of electronic heart pacemakers. More specifically the invention pertains to improvements in atrial-ventricular demand pacemakers to improve their operation by decreasing the possibility that an atrial stimulation pulse artifact will be sensed as a ventricular depolarization by the sense amplifier of the ventricular demand circuitry of the pacemaker.

BACKGROUND OF THE PRIOR ART

Of the numerous different types of electronic heart pacemakers and their corresponding various modes of operation which have been proposed in the art, the present invention is primarily directed to atrial-ventricular sequential pacemakers operating on a demand basis, either in an implantable or external device. In a demand type pacemaker, a predetermined minimum heart beat rate is established, with its corresponding maximum interval between successive heart beats. The minimum heart beat rate itself may be adjustable or programmable as is generally known in the art, but once it is set the pacemaker will operate in accordance with the selected or programmed rate. So long as the rate of the heart remains above the minimum rate, the stimulating pulse generating circuits are inhibited or reset and the pacemaker does not deliver any stimulating pulses to the heart. However, if the time interval between successive heart beats becomes greater than the selected amount corresponding to the minimum rate, the pacemaker delivers a stimulating pulse to the heart so as to support the heart at or above the preselected minimum rate. In order to provide the demand mode of operation, sensing means are provided for detecting a spontaneous ventricular depolarization. The sensing means generally includes a sense amplifier having an input connected to the ventricular stimulating electrode so that the electrical activity associated with a ventricular depolarization is picked up by the ventricular electrode and conveyed back to the pacemaker where it is applied to a sense amplifier. The sense amplifier generally contains electrical filtering networks which tailor the frequency of response of the amplifier for good sensitivity to the QRS wave complex of the electrocardiogram while rejecting other portions of the electrocardiogram.

Additionally, in the case of an atrial-ventricular pacemaker, the sense amplifier must be capable of rejecting the atrial stimulating pulse delivered by the pacemaker. The atrial stimulation pulse, delivered by the pacemaker through a separate lead to the atrium of the heart, may be conducted through body tissues and picked up by the ventricular lead, from which it is conducted to the sense amplifier. The magnitude of the atrial pulse thus picked up is typically many times that of the QRS wave, complicating the design of the sense amplifier discriminating circuits. Usually, a combination of electronic filtering to adjust the frequency response of the sense amplifier and establishing a minimum lead separation between the locations of the atrial and ventricular stimulation electrodes in the heart is required for proper operation. Unfortunately, this may require tuning the frequency response of the sense amplifier to less than optimum for the QRS wave in order to provide adequate rejection of the atrial pulse. A further disadvantage is that lead separation of electrodes within the heart may be difficult to achieve and maintain, especially if there is a possibility that a lead may be dislodged or moved slightly subsequent to the implantation.

SUMMARY OF THE INVENTION

In order to overcome these and other problems, the present invention provides for blanking the sense amplifier during delivery of an atrial pulse so that it will not be affected thereby. The blanking is achieved through switching circuits generating in timed relationship with the atrial pulse. Holding circuit means are provided for maintaining an average input signal value at the input of the sense amplifier during the blanking interval, and for smoothing the transition between normal and blanked operation of the amplifier so as to prevent switching transients caused by the blanking process itself from affecting the operation of the sense amplifier. The holding circuit is preferably held until after the atrial pulse has ended and the other switching circuits have returned to normal, to prevent switching artifact from getting into the sense amplifier. In the case of a dual demand pacemaker, the blanking technique can be applied also to the sense amplifier for the atrial pulse generator, to prevent unwanted ventricular pulse artifact from affecting it.

BRIEF DESCRIPTION OF THE DRAWING

In the drawing, FIG. 1 is a block diagram of an atrial-ventricular pacemaker using the blanking technique of the present invention;

FIG. 2 is a schematic diagram of a first embodiment of a blanking circuit according to the present invention;

FIG. 3 is a chart illustrating pertinent operating waveforms for the embodiment of FIG. 2;

DETAILED DESCRIPTION OF THE PREFERRED EMBODIMENT

Figure 4:
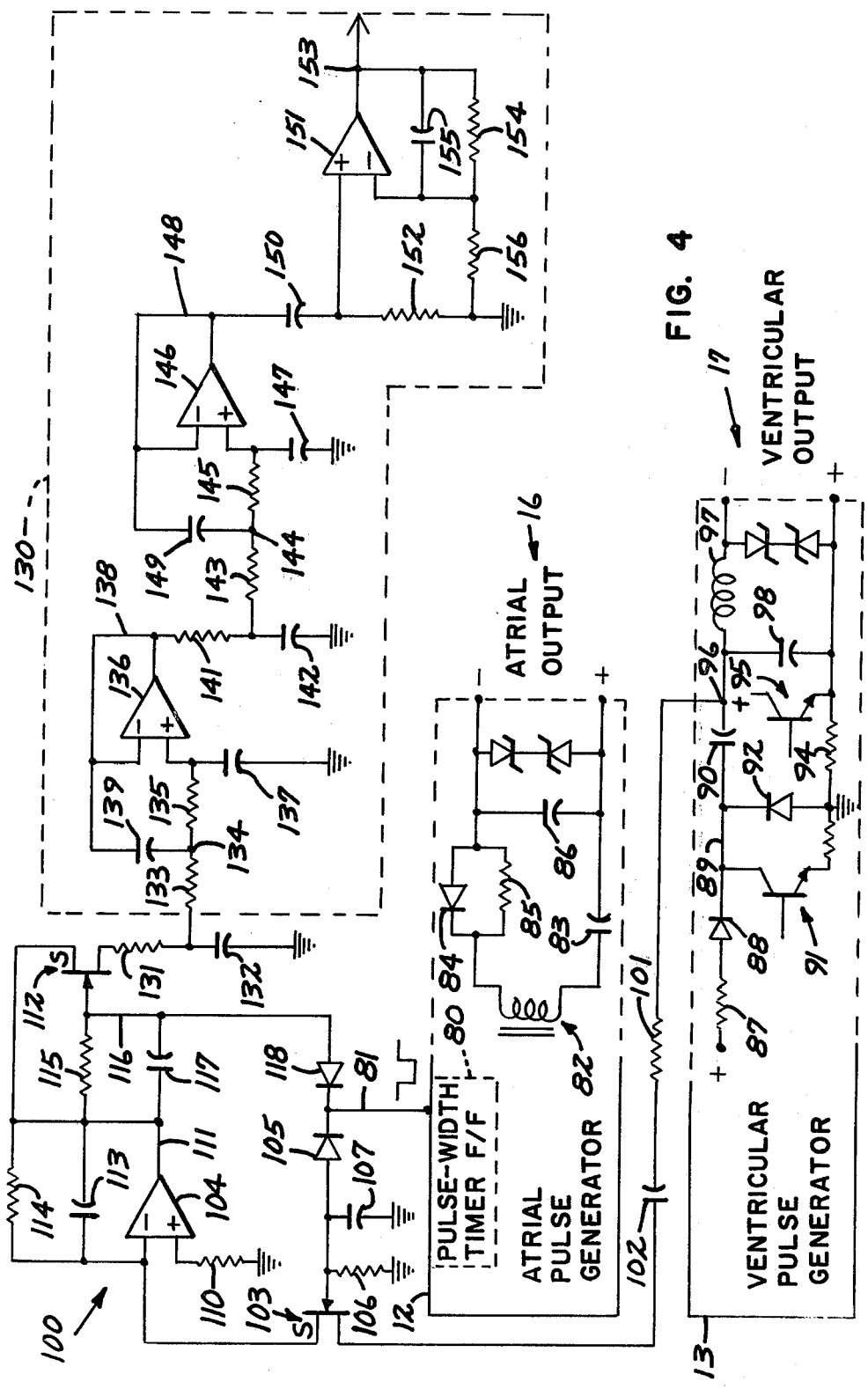
FIG. 4 is a schematic diagram of a second embodiment of a blanking circuit according to the present invention, including the pulse output circuits of the pacemaker.

Referring to FIG. 1, reference number 10 generally designates a pacemaker incorporating the present invention, and reference number 11 generally designates a heart to be paced by pacemaker 10. Pacemaker 10 includes atrial pulse generator 12 and ventricular pulse generator 13. As is generally known in the art, these generators are designed to provide output stimulating pulses for the atrium and ventrical respectively. Means are provided, as suggested by interconnection 14, for synchronizing generators 12 and 13 to provide the appropriate A-V delay interval. Output terminals 16 and 17 are provided, connected respectively to the outputs of the generators 12 and 13. Lead 18 extends from connector 16 for placement within the atrium of the heart with the electrode at its tip placed for atrial stimulation. Lead 19 extends from connector 17 into the ventrical of the heart with the electrode at its tip placed for ventricular stimulation of the heart.

Within pacemaker 10, conductor 20 is provided from connector 17 for conveying signals picked up by ventricular lead 19 to the sense amplifier, for use in demand mode operation. However, instead of connecting conductor 20 directly to sense amplifier 21, a blanking circuit 30 is provided at the input thereof. Conductor 20 connects to an input of blanking circuit 30, and the output of blanking circuit 30 is connected by a conductor 22 to sense amplifier 21. Synchronizing signals for blanking circuit 30 are provided on conductor 15 from atrial pulse generator 12. The output of sense amplifier 21 connects via conductor 23 for control of the ventricular and atrial pulse generators as is generally known in the art for demand type pacemakers.

Referring now to FIG. 2, a first embodiment of the blanking circuit 30 is shown. Conductor 20 connects through a series resistance 31 and capacitor 32 to a conductor 33. A pair of clamping diodes 34 and 35 are connected in opposite polarity between conductor 33 and signal ground. Conductor 33 also connects to one terminal of a field effect transistor (FET) 36 whose other terminal connects to conductor 37 and whose gate is connected to conductor 38. Another FET 40 is connected between conductor 37 and signal ground, and its gate is connected to conductor 41. A resistor 42 also connects from conductor 37 to signal ground. A third control FET 43 is connected between conductor 37 and conductor 44, with its gate connected to conductor 45. A capacitor 46 connects from conductor 44 to signal ground, and conductor 44 connects to the inverting input of an operational amplifier 47 which is provided for isolation, or alternatively, which may be the initial stage of the sense amplifier. The output of operational amplifier 47 is connected to conductor 22 which leads to the sense amplifier. Feedback resistor 48 and resistor 49 connected to the non-inverting input of amplifier 47 are provided for adjusting the gain thereof.

Conductors 38, 41 and 45 apply the control signals "A", "B" and "C" shown in FIG. 3 for controlling the blanking operation of the circuit. These three control signals have waveforms as shown in FIG. 3, and they are generated by the following circuitry in FIG. 2.

In FIG. 2 the atrial pulse generator 12 is further broken down to the atrial output stage 50, which provides the atrial stimulation pulses as generally known in the prior art, and additional circuitry for providing synchronizing signals for use by the blanking circuit. A master atrial pulse generator 51 is provided to generate the timing signals for use by the atrial output stage, but these pulses are delayed slightly in order to enable the blanking circuit to initiate its blanking operation just prior to the delivery of an atrial output pulse. Of course the master pulse generator 51 would be synchronized with the ventricular pulse generator through conventional means not shown, but also taking into account the delay between the master pulse generator 51 and atrial output stage 50, in order to provide the predetermined A-V delay interval.

As seen in the top line of FIG. 3, master pulse generator 51 delivers an output pulse "M" having a duration of 1,000 microseconds, and the pulse is repeated as required according to the pacing interval of the pacemaker. Only one such pulse is shown in FIG. 3. The output of pulse generator 51 which delivers the master pulse "M" is connected by conductor 52 to a delay circuit which includes series resistor 53 and shunt capacitor 54 which connects to signal ground. The time constant of this resistance-capacitance combination is selected to provide a 100 microsecond delay. A pair of Schmitt triggers 55 and 56 are connected in series from this timing circuit to square the pulses and restore logic levels. The output of these Schmitt triggers at conductor 57 is the atrial output pulse "O" which is fed to the atrial output stage 50. The output pulse "O" is shown in the second line of FIG. 3 to be a pulse also having a duration of 1,000 microseconds, with both its leading and trailing edges delayed by 100 microseconds with respect to master pulse "M".

A branch of conductor 52 connects through a diode 60 to an RC timing circuit consisting of resistor 61 and shunt capacitor 62. This timing circuit is chosen to have a time constant of 200 microseconds, and the output thereof is fed through an inverting Schmitt trigger 63 to provide control "A" at conductor 38 of FIG. 2. Control "A" is shown in the third line of FIG. 3 as a normally high logic level which switches low at the beginning of a master pulse "M" and remains low for an interval of approximately 200 microseconds following the termination of the master pulse "M", at which time it returns to its normally logical high level.

A branch of conductor 57 of FIG. 2 connects through a diode 64 to the input of a unity gain buffer amplifier 65. Parallel resistor 66 and capacitor 67 also connect from the input of this amplifier to signal ground, and these components are chosen to have a time constant of approximately 500 microseconds. The output of amplifier 65 connects to control conductor 41 to convey the "B" control which is shown in the fourth line of FIG. 3. As the output pulse "O" goes to a logic one level, this level is conveyed through diode 64 and buffer amplifier 65, with capacitor 67 charging essentially instantaneously for purposes of the timing considerations of the pulses in FIG. 3. Control "B" therefore goes to a logical high level essentially with pulse "O". At the termination of pulse "O", control "B" returns gradually to the logical low level as capacitor 67 discharges through resistor 66 over its approximately 500 microsecond time constant.

A branch of conductor 52 of FIG. 2 which carries the "M" master pulse connects through a diode 70 to an inverter 71. Parallel shunt resistor 72 and capacitor 73 are connected in series from the input of inverter 71 to signal ground. These components are chosen to have a time constant of approximately 500 microseconds. The output of inverter 71 connects to the cathode of a diode 74, the anode of which connects to conductor 45. A biasing resistor 75 connects from conductor 45 to a positive logic level indicated by the symbol "+", and a capacitor 76 connects from conductor 45 to signal ground. Resistor 75 and capacitor 76 are chosen to provide a time constant of approximately 500 microseconds.

Control "C" is shown in the bottom line of FIG. 3. As the master pulse "M" goes to its high logic level, control signal "C" switches from its normally high level to a logical low level, due to the action of inverter 71. At the end of master pulse "M", signal "C" remains low due to the maintenance of the logical high level at the input of inverter 71 by capacitor 73. Capacitor 73 begins to discharge through resistor 72 and at approximately 500 microseconds later is reduced to sufficiently low value that inverter 71 changes states. It will be apparent to those skilled in the art that the actual component values for resistor 72 and capacitor 73 would be chosen in connection with the voltage level at which inverter 71 changes states in order to provide the desired 500 microsecond delay. After this interval, the output of inverter 71 switches to a high level, but this is blocked by diode 74 and the actual voltage at conductor 45 slowly charges up to the high level as capacitor 76 is charged through resistor 75. Thus, the low logic level for control "C" remains low after the termination of master pulse "M" and atrial output pulse "O" and then gradually returns to the normal logical high level.

In normal operation other than during delivery of an atrial pulse by the pacemaker, the circuit of FIG. 2 serves to couple electrical signals from the heart to the sense amplifier for use in demand mode operation. Resistor 31 and capacitor 32 serve as coupling elements from the ventricular lead. Diodes 34 and 35 clip the ventricular output pulse to minimize its effect upon the sense amplifier. In normal operation FET 36 is on, FET 40 is off, and FET 43 is on so that signals from conductor 33 are conveyed to conductor 44 and amplifier 47. In this mode of operation, resistor 42 and capacitor 46 comprise an RC timing network. The output of amplifier 47 on conductor 22 is connected to the sense amplifier, which operates in the conventional manner to discriminate the QRS wave complex to detect ventricular depolarizations. Amplifier 47 is primarily used as a buffer amplifier in FIG. 2. As previously mentioned, it could be replaced or integrated into the input amplifier circuits of the sense amplifier, in which case the time constant of resistor 42 and capacitor 46 could also be selected in consideration of the overall frequency response tailoring of the sense amplifier in order to economize on the number of components utilized in the overall pacemaker circuit.

Upon delivery of an atrial pulse by the pacemaker, the circuitry of FIG. 2 blanks or decouples the sense amplifier from the ventricular lead, while providing a stored input reference voltage to the sense amplifier to avoid abrupt switching transients either at the beginning of the ending of the blanking. This is accomplished as follows, with reference to FIG. 2 and FIG. 3.

Just prior to the start of the atrial output pulse, FET 36 is turned off by control "A". This effectively places a high impedance in the signal path between conductors 33 and 37 to isolate the sense amplifier from the ventricular lead. At the same time, FET 43 is turned off, inserting another high impedance in the signal path, between conductors 37 and 44 to further isolate the sense amplifier. In addition, turning off FET 49 isolates capacitor 46 from its discharge path through resistor 47 (it being assumed that the input impedance to amplifier 47 is so high as to be infinite for all practical purposes). Whatever voltage existed at conductor 44 just prior to the start of a master pulse "M" is now held and continued to be applied through amplifier 47 to the sense amplifier.

FET 40 is switched on after FET 36 has been switched off. For convenience, this can be accomplished at about the time of the beginning of the atrial output pulse "O", which is about 100 microseconds after the switching of FET 36. This provides a low impedance path to ground for conductor 37 which, in conjunction with the high impedance series path presented by FET 36, further helps to isolate the sense amplifier during the blanking interval. FET 40 is also used at the end of the blanking period to provide a discharge path for capacitor 32 prior to fully reconnecting the sense amplifier to the ventricular lead.

FET 40 remains on at the end of the atrial output pulse "O", but is gradually returned to its off condition over the next approximately 500 microseconds or so by control "B". Control "A" returns to a high level approximately 100 microseconds after the end of the atrial pulse to turn FET 36 back on, while FET 40 is also still on. This permits any charge which may have accumulated across capacitor 32 due to signals applied from the ventricular lead during the blanking interval to be discharged prior to reconnection to the sense amplifier. FET 43 remains off while FET's 36 and 40 are being returned to their normal state as described above, so that any switching transients associated therewith will not be applied to the sense amplifier. FET 43 is subsequently gradually turned back on by control "C", and this gradual turning on together with the integrating effect of capacitor 46 ensures that the new analog signal at conductor 20 will be gradually and smoothly applied to the sense amplifier. The circuit of FIG. 2 remains in the normal or unblanked condition in which it transmits any electrical activity picked up by the ventricular lead 19 to the sense amplifier, until such time that the next atrial stimulation pulse occurs, at which time the blanking process described above is repeated.

The preferred embodiment of the atrial pulse blanking circuit is shown in FIG. 4, in which reference number 100 generally designates the blanking circuit, reference number 130 generally designates the active filter input section of the sense amplifier of an A-V demand pacemaker, and reference numbers 12 and 13 indicate the atrial and ventricular pulse generators, respectively. Pulse generators 12 and 13 are shown partially in block diagram form, except that their output circuits are shown in schematic diagram form, since certain aspects thereof are important for optimum operation as is discussed in further detail below.

Pulse generator 12 includes a pulse width timer indicated by reference number 80. This refers to the circuit or circuits of the atrial pulse generator responsible for the actual initiation and termination of the atrial pulse to be developed and delivered by the generator. The output of this circuit 80 is provided at conductor 81 where it is used for timing purposes for the blanking circuit. Of course, the output of circuit 80 is also used internally within the atrial pulse generator 12 as is generally known in the art to effect the generation of the atrial output pulse. In the embodiment shown, the signal at conductor 81 is normally a logically high signal, which goes low during the duration of an atrial pulse, after which it returns to its normally high state. The output circuit of generator 12 includes a pulse transformer 82, the secondary of which is shown in FIG. 4, connecting at one branch thereof through a capacitor 83 to the plus terminal of atrial output terminal 16. The other branch of the secondary transformer 82 connects to the cathode of a diode 84 and to a resistor 85 which is connected in parallel with diode 84. The other side of resistor 85, together with the anode of diode 84 are connected to the minus terminal of atrial output terminal 16. A capacitor 86 for r.f. interference rejection connects between the output plus and minus terminals, as do a pair of opposed Zener diodes which are provided for overvoltage protection.

The output circuit of ventricular pulse generator 13 is of the constant-current type, although a constant-voltage type circuit could also be used. The output circuit includes a resistor 87 which connects from the power supply for the circuit, indicated by the plus symbol, to the anode of a diode 88. The cathode of diode 88 connects to a conductor 89. Conductor 89 connects to a capacitor 90, the collector of a transistor 91, and the cathode of a diode 92, the anode of which connects to signal ground. The emitter of transistor 91 connects through a resistor 93 to signal ground. The plus terminal of ventricular output terminal 17 connects to a resistor 94, the other side of which connects to signal ground. A transistor 95 is connected with its emitter to the plus terminal of ventricular output 17 and its collector to the plus voltage supply. Transistors 91 and 95 are switching transistors for the constant-current type output circuit, and they together provide voltage doubling to increase compliance of the output current source. The other connections of transistors 91 and 95 to the circuitry of pulse generator 13 have been omitted from the drawing for purposes of clarity. The other side of capacitor 90 connects to a conductor 96. An inductor 97 connects between conductor 96 and the minus terminal of ventricular output terminal 17. A capacitor 98 connects between conductor 96 and the plus terminal of ventricular output 17, components 97 and 98 being provided for r.f. interference rejection. A pair of opposed Zener diodes connect between the plus and minus terminals of the output.

A branch of conductor 96 connects through series connected resistor 101 and capacitor 102 to the drain terminal of an FET transistor 103. The source terminal of FET 103 connects to the inverting input of an operational amplifier 104. The gate terminal of FET 103 connects through diode 105 to conductor 81. Resistor 106 and capacitor 107 are connected in parallel from the gate of FET 103 to signal ground.

The non-inverting input of operational amplifier 104 connects through a resistor 110 to signal ground. The output of operational amplifier 104 connects to a conductor 111, a branch of which connects to the source terminal of FET 112. A capacitor 113 and a resistor 114 are connected in parallel from output conductor 111 to the inverting input of operational amplifier 104. A resistor 115 connects between conductor 111 and a further conductor 116, a branch of which connects to the gate of FET 112. Capacitor 117 also connects between conductors 111 and 116. A branch of conductor 116 connects through diode 118 to conductor 81.

Resistor 131 and capacitor 132 are connected in series between the drain terminal of FET 112 and signal ground. A resistor 133 connects from the junction of components 131 and 132 to a conductor 134. A resistor 135 connects from conductor 134 to the non-inverting input of an operational amplifier 136, and also to a capacitor 137, whose other side connects to signal ground. The output of operational amplifier 136 connects to a conductor 138, a branch of which leads back to the inverting input of amplifier 136. A capacitor 139 connects between conductors 138 and 134.

A second stage of the active filter comprises an operational amplifier and associated components 141–149 which are connected in the same manner as components 131–139 previously described, with the resistor 141 connecting from the output of operational amplifier 136. The output of operational amplifier 146 at conductor 148 connects through a capacitor 150 to the non-inverting input of a further operational amplifier 151. A resistor 152 is connected between signal ground and the non-inverting input. The output of amplifier 151 connects to a conductor 153. Resistor 154 and capacitor 155 are connected in parallel between conductor 153 and the inverting input of amplifier 151. A resistor 156 connects from the inverting input to signal ground. A branch of conductor 153 connects to the remaining of the sense amplifier circuitry (not shown) as is generally known for sensing ventricular depolarizations and for controlling the atrial and ventricular pulse generators in response thereto in demand operation.

In operation of the embodiment of FIG. 4, atrial pulse generator 12 and ventricular pulse generator 13 operate in the conventional manner to provide timed sequential atrial and ventricular stimulating pulses to the heart, except that pulse delivery is inhibited by conventional demand control circuitry (not shown) in the event of the occurrence of a spontaneous ventricular depolarization. During normal operation of the circuitry of FIG. 4 at times other than during the delivery of an atrial pulse, electrical signals from the heart are picked up by the ventricular electrode lead and are conveyed from ventricular output terminal 17 through blanking circuit 100, which serves as a preamplifier as well as a blanking circuit, to the active filter 130 at the input of the sense amplifier for the demand control circuitry (not shown). Specifically, electrical signals from the ventricular region of the heart are conveyed over the ventricular lead to the negative terminal of terminal 17 through inductor 97, conductor 96, resistor 101 and coupling capacitor 102 to FET 103. During intervals when atrial pulse generator 12 is not producing an output pulse, the voltage at lead 81 remains high, and both FET's 103 and 112 are on. Amplifier 104 and associated circuitry including the input time constant of C102 and R101 form a short time constant differentiator that serves as a preamplifier to the sense amplifier. Capacitor 113 rolls off the high frequency response. The primary frequencies of interest are at about 10 hertz, and a differentiator has the advantage of responding more to the slopes of signals, not slow long term drifts.

During the unblanked time period, signals are applied to the input and signals from the output at 111 pass through FET 112 to the active filter 130 and to the sense amplifier. In the preferred embodiment, active filter 130 is a six pole active filter designed to optimize response of the sense amplifier to the QRS wave complex of the electrocardiogram while rejecting other signals. When a ventricular depolarization is thus detected, conventional circuitry within the sense amplifier (not shown in FIG. 4 but indicated by reference 21 in FIG. 1) functions to reset the pulse generators.

During the time of delivery of an atrial stimulating pulse by generator 12, blanking circuit 100 prevents the atrial output pulse from being picked up and passed to the sense amplifier where it could mistakenly be sensed as a ventricular depolarization, which would disrupt the intended operation of the pacemaker as discussed above. Just prior to the start of the atrial output pulse, pulse width timer 80 changes states, going to a logical low signal. This signal applied through diodes 105 and 118 turns off both FET's 103 and 112. FET 103 then serves as an input series blanking switch which keeps the atrial pace pulse artifact from getting into the preamplifier and disturbing its quiescent point. At the same time FET 112 serves as an output track-and-hold switch. During the blanking interval FET 112 prevents any switching transients or other artifact caused by the blanking process from getting out of the preamplifier stage and into filter 130. At the same time, FET 112 in conjunction with resistor 131 and capacitor 132, which form a low-pass RC filter, store and hold the signal value existing just prior to the blanking process so that no abrupt signal transition is applied to the input of filter 130 during the blanking process.

At the end of the atrial pulse control line 81 returns to its logical high state. However, due to the action of capacitor 107 and resistor 106 FET 103 remains off for about 800 microseconds following the end of the atrial pulse. Resistor 115 and capacitor 117 are chosen to keep FET 112 off for about 9 milliseconds following the termination of the atrial pulse. These time delays are selected to give good immunity to atrial pulse artifact while providing minimum disruption to the input of the sense amplifier, and so that the blanking interval will be kept to a reasonably short interval.

While the addition of blanking circuit 100 gives some improvement in atrial output artifact rejection, it has been discovered that optimum performance requires certain modifications in the atrial and ventricular output circuits. Following an atrial output pulse, the post-pulse recharge current within the atrial output circuit produces a signal which will be picked up by the ventricular lead and applied to the sense amplifier. This recharge current signal is of much lower amplitude than the atrial output pulse, but it is of a much longer duration, making it difficult to blank out. Also, the recharge current signal has frequency components that fall in the same band as the physiologically generated QRS signals sought to be detected, which rules out the possibility of filtering out the recharge current signal.

The post-atrial pulse recharge current artifact can be controlled by the addition of resistor 85 and diode 84 in the output circuit of the atrial pulse generator. As compared with a prior art circuit where the negative terminal of the atrial output 16 connects directly to a branch of the secondary of transformer 82, the inclusion of resistor 85 effectively limits the recharge current. Diode 84 bypasses resistor 85 during the atrial pulse. In connection with adding resistor 85, the atrial output capacitor 83 was reduced in value to hold the atrial recharge time constant at a reasonable value of approximately 0.44 seconds in the preferred embodiment.

Additional atrial artifact rejection can be achieved by modifications in the ventricular output circuitry. The atrial pacing signal drives current into the ventricular output thereby causing ventricular lead depolarization which in turn might affect the sense amplifier. Increasing the resistance of output recharge resistor 87 effectively limits the amount of current driven into the ventricular output circuit, thereby reducing the amount of ventricular lead depolarization induced by the atrial pulse artifact. In the preferred embodiment, the rcharge resistor 87 was increased from 4.7 kilohms to 10 kilohms. Output capacitor 90 was reduced to hold the recharge time constant at a reasonable value of approximately 0.22 seconds. Further it has been found that a single output capacitor 90 can be used instead of back-to-back output capacitors that were used in a prior art circuit.

The presently preferred embodiment of the circuit of FIG. 4 includes the following components.

| | |
|---|---|
| R85 | 20 kilohm |
| R87 | 10 kilohm |
| C90, C83 | 22 microfarad |
| R101 | 30 kilohm |
| C102 | .01 microfarad |
| R106 | 390 kilohm |
| C107 | 1000 picofarad |
| R110, R114 | 4.3 megohm |
| C113 | 390 picofarad |
| R115 | 750 kilohm |
| C117 | 6800 picofarad |
| R131, 133, 135 141, 143, 145 | 82 kilohm |
| C132, 137 | .039 microfarad |
| C139 | .33 microfarad |
| C142 | .022 microfarad |
| C147, 155 | 0.1 microfarad |
| C149 | .056 microfarad |
| C150 | .02 microfarad |
| R152, 154 | 100 kilohm |
| R156 | 200 ohms |
| Transistors 103, 112 | 2N 4338 |

Operational Amplifiers 104, 136, 146, 151: Texas Instruments TL064 or equivalent.

A circuit built according to the above preferred embodiment produces superior results in terms of atrial output pacing artifact rejection, even with large atrial output signals and minimum atrial and ventricular lead separation. While the above presently preferred embodiment gives satisfactory performance, it will be understood that additional circuit changes can be made depending upon the type of pacemaker, circuitry involved. For example, input blanking FET switch 103 and associated components could be eliminated, and sense output FET switch 112 would still provide blanking of the output from the preamplifier, to provide satisfactory operation. Also, the turn-on time delay to FET switch 112 could be shortened, and the changes in the values in the ventricular and atrial output circuits could also be varied while still maintaining satisfactory operation, and in any event improved operation over a pacemaker circuit with no atrial pulse blanking or recharge current limiting. While the preferred embodiment shown uses bipolar outputs of the pulse generators, the invention is applicable to pacemakers using unipolar outputs also.

As mentioned above, the invention can be used with a dual demand pacemaker, in which case an additional blanking circuit would be used between the atrial output terminal and the input to the additional sense amplifier that controls resetting of the atrial pulse generator in a dual demand pacemaker. The component values and time constants would be altered, of course, for the additional blanking circuit and sense amplifier, so that the desired result of sensing atrial depolarizations while rejecting ventricular pulse artifact would be achieved, along with the atrial artifact rejection as described above.

What is claimed:

1. A heart pacemaker comprising:
   terminal means for connection to a patient's means for delivery atrial and ventricular stimulation thereto;
   generating means for delivering sequential atrial and ventricular electrical stimulation pulses to said terminal means at a predetermined repetition rate;
   a sensing amplifier for sensing electrical signals indicative of the patient's heartbeat;
   blanking means for normally connecting said terminal means to said sensing amplifier for conveying the patient's heartbeat signals thereto, and for selectively decoupling said sensing amplifier from said terminal means during delivery of an atrial stimulation pulse, said blanking means including holding circuit means operative during a blanking interval to hold a prior signal level at the input to the sensing amplifier, and timing means for sequentially returning the blanking means and the holding means to normal operation at the end of the atrial stimulation pulse.

2. A heart pacemaker comprising:
   terminal means for connection to a patient's heart for delivering atrial and ventricular stimulation thereto;

generating means for delivering sequential atrial and ventricular electrical stimulation pulses to said terminal means at a predetermined repetition rate;

a sensing amplifier for sensing electrical signals indicative of the patient's heartbeat;

demand control means connected to said sensing amplifier and operative for preventing delivering of said stimulating pulses if a heartbeat occurs within a predetermined time interval following a preceding heartbeat;

means for providing a signal path from said terminal means to said sensing amplifier, said signal path means including a first switching means for selectively preventing the passage of signals along the signal path;

signal holding means including a capacitor connected to said signal path means between said switching means and the sensing amplifier, and a second switching means operatively connected to selectively isolate said capacitor from said signal path and said first switching means and to thereby hold a prior signal at the input of said sensing amplifier; and timing means operatively connected for actuating said first and second switching means during delivery of an atrial pulse to block said signal path and hold a prior signal at said sensing amplifier, whereby atrial pulse artifact is prevented from entering the sense amplifier.

3. A heart pacemaker according to claim 2 wherein said first switching means comprises a series switching element connected in series with said terminal means and said sensing amplifier and a shunt switching element connected between said signal path and signal ground both selectively operative in response to said timing means for blocking the passage of signals along said signal path.

4. A heart pacemaker according to claim 2 wherein said signal holding means includes a shunt capacitor connected between the signal path and signal ground and a shunt resistor connected between said signal path and signal ground to form a discharge path for said capacitor, with said second switching means connected in series in said signal path between said resistor and said capacitor.

5. A heart pacemaker according to claim 2 wherein said timing means includes means for actuating said first and second switching means just prior to delivery of an atrial pulse.

6. A heart pacemaker according to claim 2 wherein said timing means includes means operative at the end of an atrial pulse for delaying the return of said second switching means to normal operation until after the return of said first switching means to normal operation, to prevent switching artifact from entering said sensing amplifier.

7. A heart pacemaker comprising:

terminal means for connection to a patient's heart for delivering atrial and ventricular stimulation thereto;

generating means for delivering sequential atrial and ventricular electrical stimulation pulses to said terminal means at a predetermined repetition rate;

a sensing amplifier for sensing electrical signals indicative of the patient's heartbeat;

demand control means connected to said sensing amplifier and operative for preventing delivery of said stimulating pulses if a heartbeat occurs within a predetermined time interval following a preceding heartbeat;

blanking means for normally connecting said terminal means to said sensing amplifier for conveying the patient's heartbeat signals thereto, and for selectively decoupling said sensing amplifier from said terminal means during delivery from said terminal means during delivery of an atrial stimulation pulse, said blanking means including holding circuit means operative during a blanking interval to hold a prior signal level at the input to the sensing amplifier.

8. A heart pacemaker according to claim 7 wherein said blanking means includes timing means for sequentially returning the blanking means and the holding means to normal operation at the end of the atrial stimulation pulse.

* * * * *